United States Patent
Kansal (10) Patent No.: US 9,084,649 B2
(45) Date of Patent: Jul. 21, 2015

(54) ORTHODONTIC SEPARATOR

(76) Inventor: Sudhanshu Kansal, Delhi (IN)

(*) Notice: Subject to any disclaimer, the term of this patent is extended or adjusted under 35 U.S.C. 154(b) by 0 days.

(21) Appl. No.: 13/982,677

(22) PCT Filed: Jan. 30, 2012

(86) PCT No.: PCT/IN2012/000065
§ 371 (c)(1),
(2), (4) Date: Jul. 30, 2013

(87) PCT Pub. No.: WO2012/104868
PCT Pub. Date: Aug. 9, 2012

(65) Prior Publication Data
US 2013/0302744 A1    Nov. 14, 2013

(30) Foreign Application Priority Data
Feb. 3, 2011    (IN) .............................. 257/DEL/2011

(51) Int. Cl.
*A61C 7/00*    (2006.01)
*A61C 5/12*    (2006.01)

(52) U.S. Cl.
CPC .. *A61C 7/00* (2013.01); *A61C 5/127* (2013.01)

(58) Field of Classification Search
CPC ........ A61C 5/122; A61C 5/125; A61C 5/127; A61C 7/00; A61C 7/02; A61C 7/10; A61C 7/36; A61C 7/146; A61C 2007/00
USPC ................. 433/2, 3, 7, 18, 21, 23, 24, 34, 37, 433/39–41, 138, 139, 148, 149
See application file for complete search history.

(56) References Cited

U.S. PATENT DOCUMENTS

| | | | |
|---|---|---|---|
| 1,829,898 A * | 11/1931 | Ivory | 433/149 |
| 3,052,029 A | 9/1962 | Wallshein | |
| 3,231,976 A | 2/1966 | Wallshein | |
| 5,199,869 A | 4/1993 | McGann | |
| 5,314,331 A * | 5/1994 | Brosius et al. | 433/21 |
| 5,993,210 A * | 11/1999 | Godfrey | 433/159 |
| 6,325,625 B1 | 12/2001 | Meyer | |
| 6,776,616 B2 * | 8/2004 | Dryer | 433/159 |
| 2003/0194675 A1 | 10/2003 | Williams | |
| 2007/0254263 A1* | 11/2007 | McDonald | 433/149 |
| 2008/0057457 A1* | 3/2008 | Inman | 433/6 |

FOREIGN PATENT DOCUMENTS

| | | |
|---|---|---|
| DE | 41 13 154 C1 | 10/1992 |
| FR | 656 387 A | 5/1929 |
| WO | 2010/015826 A1 | 2/2010 |

OTHER PUBLICATIONS

International Search Report of corresponding International Application No. PCT/IN2012/000065, dated on May 31, 2012.

* cited by examiner

*Primary Examiner* — Ralph Lewis
(74) *Attorney, Agent, or Firm* — Global IP Counselors, LLP (57) ABSTRACT

An orthodontic separator to simultaneously separate a mesial and a distal aspect of a tooth is disclosed. The orthodontic separator has a first separating unit and a second separating unit adapted to be connected with each other through a connecting bar and the connecting bar is provided to prevent dislodgement of the orthodontic separator from the tooth.

12 Claims, 4 Drawing Sheets

ORTHODONTIC SEPARATOR

CROSS REFERENCE TO RELATED APPLICATIONS

The present application claims priority to the International patent application PCT/IN2012/000065 dated 30 Jan. 2012, titled "Orthodontic Separator" which claims priority from Indian patent application 257/DEL/2011 dated 3 Feb. 2011 by Sudhanshu et al. and entitled "Orthodontic Separator", which is incorporated herein by references as if reproduced in its entirety.

BACKGROUND OF INVENTION

1. Field of the Invention

This invention relates to an orthodontic separator for use for creating space or gap between the teeth for the purpose of placing orthodontic bands.

2. Description of the Related Art

Orthodontic braces or dental braces are devices applied on teeth of a patient to align them and correct for any flaws of the teeth and jaws. Prior to applying the orthodontic braces on the teeth, the teeth have to be separated so that orthodontic bands can be properly fitted in between them.

Separation of the teeth is an important step in orthodontics as tight inter proximal contact makes it very difficult to properly seat the orthodontic bands. Devices used to wedge or force the teeth apart for initial tooth movement to facilitate proper fitting of orthodontic bands are called orthodontic separators. Orthodontic separators are also referred to as dental separators, dental spacers or orthodontic spacers.

Orthodontic separators are inserted in between the teeth of a patient, and kept there for a period of time to create a gap or a space between the teeth. The gap or space created is utilized to properly fit the orthodontic bands which are essential in any orthodontic treatment.

Various devices have been utilized to create the necessary space between adjacent teeth, including elastomeric modules, plastic separators, twisted brass wire, metal spring devices. One of the known devices comprises a U shaped structure having loop at the ends thereof such that to be fitted between two adjacent tooth for creating a gap there between (U.S. Pat. Nos. 3,052,029 and 3,231,976).

Another device known in the art comprises a U shaped structure having two leg segment and spring action by itself and adapted to be fitted between two tooth such that to separate them (U.S. Pat. No. 5,199,869).

Yet another device is disclosed in the U.S. Pat. No. 6,325,625 which comprises a spring yoke having tines provided at the ends of the spring yoke to facilitate wedging between two teeth. Engagement structure is provided to receive spreading instrument needed to fit the device between two teeth. Though the above devices can separate teeth for placement of orthodontic bands, but all known devices have certain inherent disadvantages.

One of the disadvantages is that one orthodontic separator can separate only one aspect of the first tooth, the mesial aspect or the distal aspect. However, to fit an orthodontic band on the first tooth such gap or space needs to be created simultaneously and adequately in both mesial as well as the distal aspect of the first tooth. Therefore, two such orthodontic separators need to be applied between the first tooth and each of its adjacent teeth to separate the mesial and distal aspect of the tooth to place one orthodontic band on the tooth.

Another disadvantage is that these orthodontic separators get dislodged from their position and can be accidently swallowed by the patient, which can be harmful, especially, if they are metal spring separators.

Yet another disadvantage is that if the orthodontic separators are loosely fitted or become loose as the separation between the teeth increases and they get embedded in gums causing gingival inflammation, bleeding gums, pain and swelling of gums.

Still another disadvantage is that premature or early dislodgement of one or more of the individual orthodontic separators can lead to insufficient separation between the teeth. The patient may have to make unproductive repetitive visits to a doctor, thereby wasting time and energy of both the patient and the doctor.

A further disadvantage is that the use of multiple orthodontic separators to create gap or space for placing orthodontic band on a single tooth is not cost effective.

Therefore, there is a need of an orthodontic separator that eliminates the disadvantages associated with the prior art orthodontic separators.

OBJECTS OF THE INVENTION

Therefore an object of the present invention is to provide an orthodontic separator which can simultaneously separate the mesial and distal aspect of the tooth for placement of orthodontic band. As the orthodontic separator in the present invention does the work of any two individual separators, hence the orthodontic separator in the present invention has a unique feature of "2 in 1" orthodontic separator.

Another object of the present invention is to provide an orthodontic separator having a connecting bar that prevents the dislodgement of a first and a second separating unit portion of the orthodontic separator and secures the orthodontic separator even after the separation is complete thereby avoiding it to get embedded in gingiva or accidental swallowing of the same. Hence, the present invention has a unique feature of "self-secured" orthodontic separator.

Yet another object of the present invention is to provide an orthodontic separator which can separate mesial and distal aspects of teeth adequately and simultaneously.

Still another object of the present invention is to provide an orthodontic separator for which the insertion and removal is fast and easy.

A further object of the present invention is to provide the orthodontic separator that is comfortable to the patient and causes no occlusal interference.

Yet another object of the present invention is to provide the orthodontic separator that is easy to construct. The orthodontic separator can be easily pre-fabricated by clinician for office use or by a company for commercial purpose.

Still another object of the present invention is to provide the orthodontic separator that can be easily adjusted in different ways according to tooth anatomy and an amount of activation required. Hence, the objective is also to provide the orthodontic separator that is very dynamic in nature.

A further object of the present invention is to provide the orthodontic separator that is economical.

STATEMENT OF THE INVENTION

According to this there is provided an orthodontic separator comprising a first separating unit and a second separating unit connected with each other through a connecting bar provided to prevent dislodgement of said orthodontic separator from the said tooth.

BRIEF DESCRIPTION OF THE DRAWINGS

An orthodontic separator according to a preferred embodiment is herein described and illustrated in the accompanying drawings wherein.

DETAILED DESCRIPTION OF THE INVENTION

An orthodontic separator is described herein below with numerous specific details so as to provide a complete understanding of the invention. However these specific details are exemplary details and should not be treated as the limitation to the scope of the invention. The terms "a" or "an", as used herein, are defined as one or more than one. The term "another", as used herein, is defined as at least a second or more. The terms "including" and/or "having" as used herein, are defined as comprising (i.e. open transition). The term "coupled" or "operatively coupled" as used herein, is defined as connected, although not necessarily directly, and not necessarily mechanically.

Figure 1:
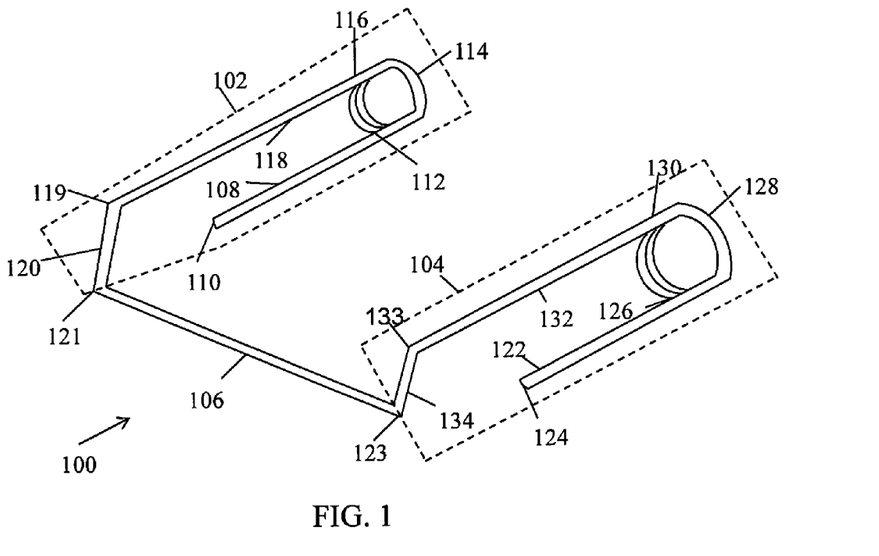
FIG. 1 illustrates an orthodontic separator, in accordance with an embodiment of the present invention.

Referring to the drawings, particularly FIG. 1 an orthodontic separator 100, in accordance with an embodiment of the present invention is shown. The orthodontic separator 100 comprises a first separating unit 102, a second separating unit 104 and a connecting bar 106 provided to connect the first and second separating units with each other. The first separating unit 102 and the second separating unit 104 are similar in action and structure and are inter-changeable according to a location of placement of the orthodontic separator 100 in the tooth in the oral cavity. In other words the first separating unit 102 could take the place of the second separating unit 104 if the location of placement of the orthodontic separator 100 is changed from an upper jaw to a lower jaw or vice versa. Similarly, the first separating unit 102 could take the place of the second separating unit 104 if the location of placement of the orthodontic separator 100 is changed from right to left side in the same jaw or vice versa.

Further, it will be readily apparent to those skilled in the art that the orthodontic separator 100 can be used for all types of teeth in the oral cavity. For example, the same orthodontic separator 100 can be used for the teeth of right or left side of upper or lower jaw as long as the teeth have similar anatomy and morphology. To illustrate further, the orthodontic separator 100 which can be used for lower jaw, left first molar can also be used for upper jaw, right side second molar.

Figure 2:
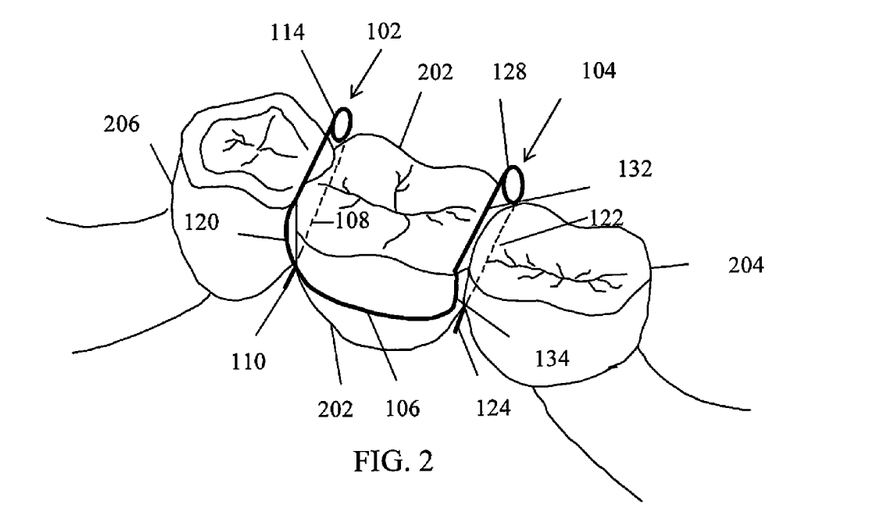
FIG. 2 illustrates the orthodontic separator placed between a tooth and adjacent teeth on either side.

In one embodiment the first separating unit 102 and the second separating unit 104 comprises a coil having a spring action. The first separating unit 102 is shown to be capable of separating a mesial aspect 600 of the tooth, for example, a tooth 202 (refer to FIGS. 2 and 3). The orthodontic separator 100 is inserted in between the teeth in a manner such that the first separating unit 102 rests along a mesial aspect 600 of the tooth 202. The first separating unit 102 is shown to include a first arm 108. The first arm 108 has a free first arm end 110 and non-free first arm end 112. The free first arm end 110 is provided to facilitate the insertion and removal of first separating unit 102 between the tooth 202 and an adjacent tooth 206 associated with the mesial aspect 600 of the tooth 202. The placement of the orthodontic separator 100 to separate the mesial 600 and the distal aspect 601 of the tooth 202 is illustrated in FIG. 2.

In one embodiment, the free first arm end 110 of first separating unit 102 is either blunted or configured to form a compressed, flat and round edged loop such that it prevents soft tissue trauma.

In one embodiment the first arm 108 runs from a lingual or palatal to a labial or a buccal aspect of the tooth 202 and is inserted below the contact area between the said tooth 202 and the adjacent tooth 206 towards the mesial aspect 600. Also, the first arm 108 may have a length substantially equal to a length of the mesial surface of the tooth 202 between the lingual/palatal and the buccal/labial surfaces. In an exemplary scenario from real life dentistry applications, the first arm 108 can have a length substantially between 6 millimeter and 9 millimeter.

It will be readily apparent to those skilled in the art that the length of the first arm 108 can be increased or decreased, either during fabrication or during insertion, according to the anatomy of the tooth, the anatomy of the adjacent tooth, the soft tissue surrounding the tooth and adjacent tooth, proper fitting of the orthodontic separator and patient's comfort.

Further, the non-free first arm end 112 of the first arm 108 is connected to a first spring coil 114. The first spring coil 114 can include one or more loops. Although the first spring coil 114 is shown to include two loops, it will be readily apparent to those with ordinary skill in the art that the exemplary orthodontic separator 100 may have a first spring coil 114 with a higher or a lesser number of coils without deviating from the scope of the invention. In an exemplary scenario from real life dentistry applications, the diameter of the first spring coil 114 can vary from 1 mm to 1.5 mm.

The first spring coil 114 provides flexibility and spring action to the orthodontic separator 100 thereby resulting in separation of the tooth 202 and the adjacent tooth 206 corresponding to the mesial aspect 600 when the first separating unit 102 of orthodontic separator 100 is inserted in between the teeth. In one embodiment the first spring coil 114 is inserted in between the teeth so as to run from a gingival to an occlusal aspect of the tooth 202. Further, the first spring coil 114 also has a first spring coil end 116. Further, in an embodiment the first spring coil 114 rests in the buccal or the labial aspect of the tooth 202 and the adjacent tooth 206.

The first spring coil end 116 is connected to a second arm 118. In one embodiment the second arm 118 runs from the buccal/labial to a lingual/palatal aspect of the tooth 202 and runs over the contact area between the tooth 202 and the adjacent tooth 206 associated with the mesial aspect 600 of the tooth 202. The second arm 118 has a length substantially equal to the length of the mesial surface between the buccal/labial and the lingual/palatal surface of the tooth 202. In an exemplary scenario from real life dentistry applications, the second arm 118 can have a length substantially between 7 millimeter and 11 millimeter.

In one embodiment the length of the second arm 118 can be substantially greater than the length of the first arm 108.

From an end of the second arm 118, i.e., the second arm end 119, initiates the first vertical step 120 and runs downwards from the occlusal aspect of the tooth 202 to the gingival aspect of the tooth 202 on the lingual or palatal aspect of the tooth 202. In an exemplary embodiment of the invention an angle between the second arm 118 and the vertical step 120 is an obtuse angle. In other embodiments the angle between the second arm 118 and the vertical step 120 can be a right angle or acute as well. In general, the angle between the second arm 118 and the vertical step 120 can be adjusted either during fabrication or during insertion according to the anatomy of the tooth. This angle is important for proper fitting, retention and activation of the orthodontic separator 100. The second arm end 119 where the angle between the second arm 118 and the vertical step 120 is formed can be rounded for patient's comfort. The first vertical step 120 preferably ends at the undercut area just below the maximum bulge or contour at the lingual or palatal aspect of the tooth 202 in order to achieve the maximum retention. The length of the first vertical step 120 depends on the anatomy of the tooth 202 and can be adjusted accordingly during fabrication and/or insertion of the orthodontic separator 100. Although the orthodontic separator 100 is shown to include a specific length of the first vertical step 120 and a specific angle between the first vertical step and the second arm 118, it will be readily apparent to those with the ordinary skill in the art that the length and the angle mentioned above can be varied without deviating from the scope of the invention.

The first vertical step is shown to end at a first vertical step 121, from where initiates a connecting bar 106 which extends horizontally from the mesial aspect 600 to the distal 601 aspect of the tooth 202 extending along the lingual or palatal aspect of the tooth 202, such that it ends at a connecting bar end 123. The connecting bar end 123 merges into a second vertical step 134. The second vertical step 134 is a part of the second separating unit 104, and its position and role will be clearer by reading the subsequent paragraphs about the second separating unit 104.

The orthodontic separator 100 is inserted in between the teeth in a manner such that the second separating unit 104 rests along a distal aspect 601 of a tooth 202. The second separating unit 104 is shown to include a fourth arm 122. The fourth arm 122 has a free fourth arm end 124 and merges into a second spring coil end 126 of the second spring coil 128. The free fourth arm end 124 is provided to facilitate the insertion and removal of second separating unit 104 between the tooth 202 and an adjacent tooth 204 associated with the distal aspect 601 of the tooth 202. The placement of the orthodontic separator 100 to separate the mesial aspect 600 and the distal aspect 601 of the tooth 202 is illustrated in FIG. 2.

In one embodiment, the free fourth arm end 124 of second separating unit 104 is either blunted or configured to form a compressed, flat and round edged loop such that it prevents soft tissue trauma.

In one embodiment the fourth arm 122 runs from a lingual or palatal to a labial or a buccal aspect of the tooth 202 and is inserted below the contact area between the tooth 202 and the adjacent tooth 204 towards the distal aspect 601. Also, the fourth arm 122 may have a length substantially equal to a length of the distal surface of the tooth 202 between the lingual/palatal and the buccal/labial surfaces. In an exemplary scenario from real life dentistry applications, the fourth arm 122 can have a length substantially between 6 millimeter and 9 millimeter.

Further, the second spring coil 128 can include one or more loops. Although the second spring coil 128 is shown to include two loops, it will be readily apparent to those with ordinary skill in the art that the exemplary orthodontic separator 100 may have a second spring coil 128 with a higher or a lesser number of coils without deviating from the scope of the invention. In an exemplary scenario from real life dentistry applications, the diameter of the coil can vary from 1 mm to 1.5 mm.

The second spring coil 128 provides flexibility and spring action to the orthodontic separator 100 thereby resulting in separation of the tooth 202 and the adjacent tooth 204 corresponding to the distal aspect 601 when the second separating unit 104 of orthodontic separator 100 is inserted in between the teeth. In one embodiment the second spring coil 128 is inserted in between the teeth so as to run from a gingival to an occlusal aspect of the tooth 202. In an embodiment the second spring coil 128 rests in the buccal or the labial aspect of the tooth 202. Further, the second spring coil 128 merges into a third arm 132 at a third arm end 130.

In one embodiment the third arm 132 runs from the buccal/labial to a lingual/palatal aspect of the tooth 202 and runs over the contact area between the tooth 202 and the adjacent tooth 204 associated with the distal aspect 601 of the tooth 202. The third arm 132 has a length substantially equal to the length of the distal surface between the buccal/labial and the lingual/palatal surface of the tooth 202. In an exemplary scenario from real life dentistry applications, the third arm 132 can have a length substantially between 7 millimeter and 11 millimeter. In one embodiment the length of the third arm 132 can be substantially greater than the length of the fourth arm 122.

The third arm 132 merges into a second vertical step 134 at a second vertical step end 133. The second vertical step 134 runs downwards from the occlusal aspect of the tooth 202 to the gingival aspect of the tooth 202 on the lingual or palatal aspect of the tooth 202. In an exemplary embodiment of the invention an angle between the third arm 132 and the second vertical step 134 is an obtuse angle. In other embodiments the angle between the third arm 132 and the second vertical step 134 can be a right angle or acute as well. In general, the angle between the third arm 132 and the second vertical step 134 can be adjusted either during fabrication or during insertion according to the anatomy of the said tooth. This angle is important for proper fitting, retention and activation of the orthodontic separator 100. The second vertical step end 133 where the angle between the third arm 132 and the second vertical step 134 is formed can be rounded for patient's comfort. The second vertical step 134 preferably ends at the undercut area just below the maximum bulge or contour at the lingual or palatal aspect of the said tooth in order to achieve the maximum retention. The length of the second vertical step 134 depends on the anatomy of the tooth and can be adjusted accordingly during fabrication and/or insertion of the orthodontic separator 100. Although the orthodontic separator 100 is shown to include a specific length of the second vertical step 134 and a specific angle between the second vertical step 134 and the third arm 132, it will be readily apparent to those with the ordinary skill in the art that the length and the angle mentioned above can be varied without deviating from the scope of the invention.

The second vertical step 134 merges into the connecting bar 106 at the connecting bar end 123.

The connecting bar 106 joins the first separating unit 102 to the second separating unit 104. In an embodiment the connecting bar 106 can join the first separating unit 102 and the second separating unit 104 in a manner so that the connecting bar 106 rests along the lingual, the palatal, the buccal or the labial aspect of the tooth 202. For the purpose of the description and ease in understanding the embodiment of the orthodontic separator 100 explained depicts the connecting bar 106 to be resting at a lingual or palatal aspect of the tooth 202.

Further, the connecting bar 106 prevents the dislodgement of the orthodontic separator 100 from the tooth 202. The connecting bar 106 preferably rests in the undercut area just below the maximum bulge or contour at the lingual or palatal aspect of the tooth 202 to enhance the retention and self-securing feature of the orthodontic separator 100. The location of the connecting bar 106 depends on the anatomy of the tooth. In an embodiment the connecting bar 106 has a length substantially equal to the mesio-distal width of a lingual or a palatal aspect of the tooth 202.

For the purpose of better understanding of construction of the orthodontic separator 100, the first separating unit 102, second separating unit 104 and connecting bar 106 are described individually in this description. However, in the embodiment represented by FIG. 1, the first separating unit 102, second separating unit 104 and the connecting bar 106 are integral part of the orthodontic separator 100 and are fabricated in continuity, for example, by using a single piece of wire. In real life dental scenario the construction may start by fabricating a pre-specified length from an end of the wire as the first arm 108, which is then bent in the form of coils after the pre-specified length to form the first coil spring 114, then subsequently bent at pre-specified lengths and in pre-defined manner to form the second arm 118, the first vertical step 120, the connecting bar 106, the second vertical step 134, the third arm 132, the second coil spring 128 and ending into the fourth arm 122.

In another embodiment [not illustrated in Figures] the connecting bar 106 can be connected to the first separating unit 102 and the second separating unit 104 at the buccal or the labial aspect of the tooth 202 and rest along the same, yet preventing the dislodgement of the first separating unit 102 and the second separating unit 104.

Examples of materials that can be used for the orthodontic separator 100 include but are not limited to nickel titanium alloy, stainless steel, plastic, elastic, rubber, and a biocompatible dental material. Similarly, examples of materials that can be used for the connecting bar 106 include but not limited to nickel titanium alloy, stainless steel, plastic, elastic, rubber, and a biocompatible dental material.

In an embodiment, the material of the connecting bar 106 is same as the material of the first separating unit 102 and the second separating unit 104. For example, all these components may be made of nickel titanium alloy.

In another embodiment, the material of the connecting bar 106 can be different from the material of the first separating unit 102 and/or the second separating unit 104. For example, the first separating unit 102 and the second separating unit 104 may be made of stainless steel and the connecting bar 106 may be made of an elastic material.

In an embodiment the gauge of a wire or any other material used to fabricate the orthodontic separator 100 can be varied, for example, within the ranges suitable for dentistry applications. Also, the wire or any other material used to fabricate the orthodontic separator 100 may have a regular round, or rectangular, irregular round/rectangular or any other cross-section.

Referring to FIG. 2 the placement of an orthodontic separator is shown. The orthodontic separator 100 in an exemplary real life dental situation where the orthodontic separator 100 is placed between the tooth 202 and adjacent teeth 206 and 204 on either side whereby the orthodontic separator 100 simultaneously separates the mesial aspect 600 and the distal aspect 601 of the tooth 202. The connecting bar 106 prevents dislodgement of the orthodontic separator 100 from the tooth 202.

Figure 3:
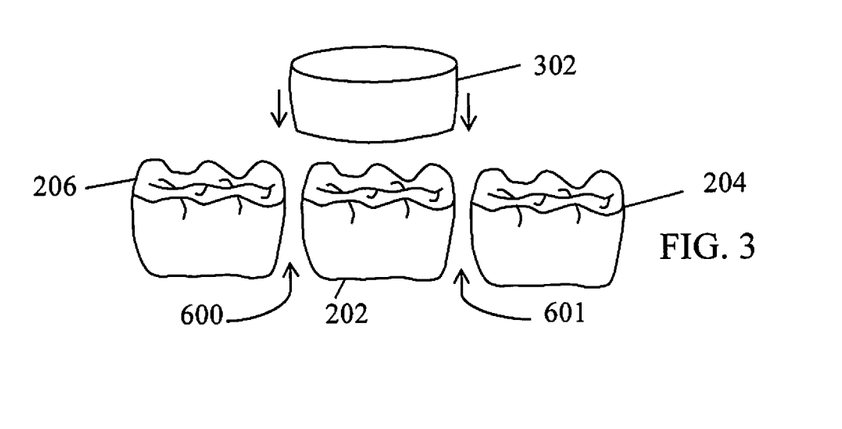
FIG. 3 illustrates a gap or space created by the orthodontic separator between the tooth and the adjacent teeth.

Referring to FIG. 3 an exemplary real life dental situation is shown where a gap or space is created by the orthodontic separator 100 between the tooth 202 and the adjacent teeth 204 and 206 so that an orthodontic band 302 can be placed on the tooth 202. In real life situations, a patient may have a dental problem that requires application of dental braces or fixed orthodontic appliance. The braces, orthodontic brackets, molar tubes and/or other orthodontic attachments etc, are spot-welded or soldered to orthodontic bands which are then cemented to the desired to teeth. The orthodontic bands provide the locations where the orthodontic braces are mounted or applied. The present invention provides solutions for creating spaces on both the aspects of the tooth for easy fitting of the orthodontic band. For example, the orthodontic band 302 can be fitted on the tooth 202 when an appropriate space is created on both the aspects of the tooth 202 by the orthodontic separator 100.

Figure 4:
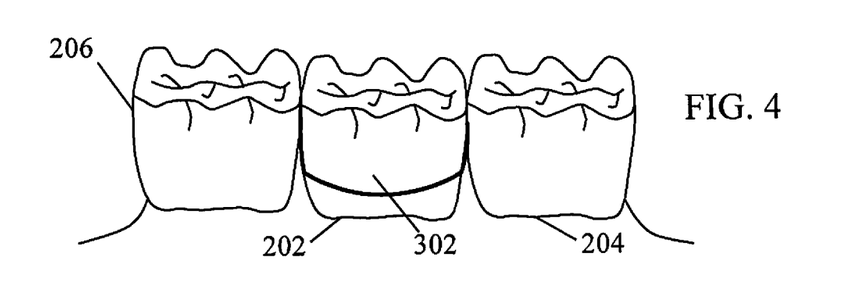
FIG. 4 illustrates an orthodontic band placed in the gap or space created by the orthodontic separator.

Referring to FIG. 4 an exemplary real life dental situation shown where the orthodontic band 302 is placed in the gap or space created by the orthodontic separator 100. The placing of the orthodontic band 302 is an important step in fixed orthodontic treatments as mentioned above.

Figure 5:
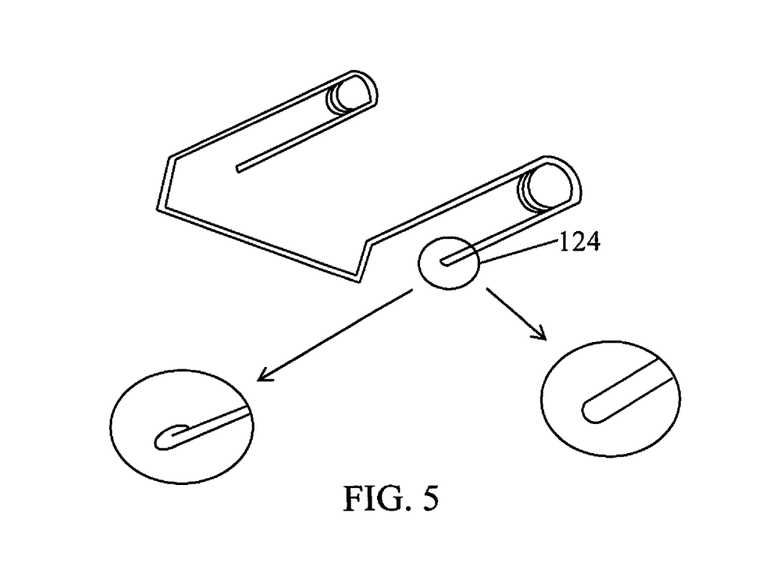
FIG. 5 illustrates embodiments of the orthodontic separator in which a free fourth arm end of the orthodontic separator is shown to be blunted or configured to form a compressed, flat and round edged loop to prevent soft tissue trauma.

Referring to FIG. 5 non-limiting and non-exhaustive exemplary embodiments of the orthodontic separator 100 is shown in which the free fourth arm end 124 is shown to be blunted or configured to form a compressed, flat and round edged loop to prevent soft tissue trauma. Although the FIG. 5 shows the free fourth arm end 124 to be blunted or configured to form a compressed, flat and round edged loop to prevent soft tissue trauma, it will be readily apparent to those with ordinary skill in the art that the free first arm end 110 can also be similarly formed. It will also be readily apparent to people with ordinary skill in the art that various different implementations can be effected to the free first arm end 110 and/or the free fourth arm end 124 to prevent soft tissue trauma without deviating from the scope of the present invention.

Figure 6:
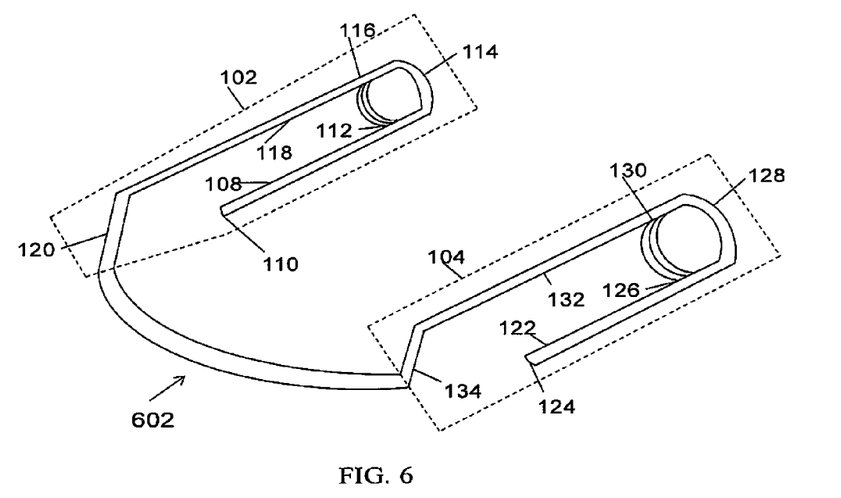
FIG. 6 illustrates another embodiment of the orthodontic separator shown in FIG. 1.

Referring to FIG. 6 an exemplary embodiment of the orthodontic separator 100 is shown, in which a connecting bar 602 is shown to be pre-contoured or capable of being contoured to adapt to the tooth 202 so as to prevent the dislodgement of the orthodontic separator 100.

Figure 7:
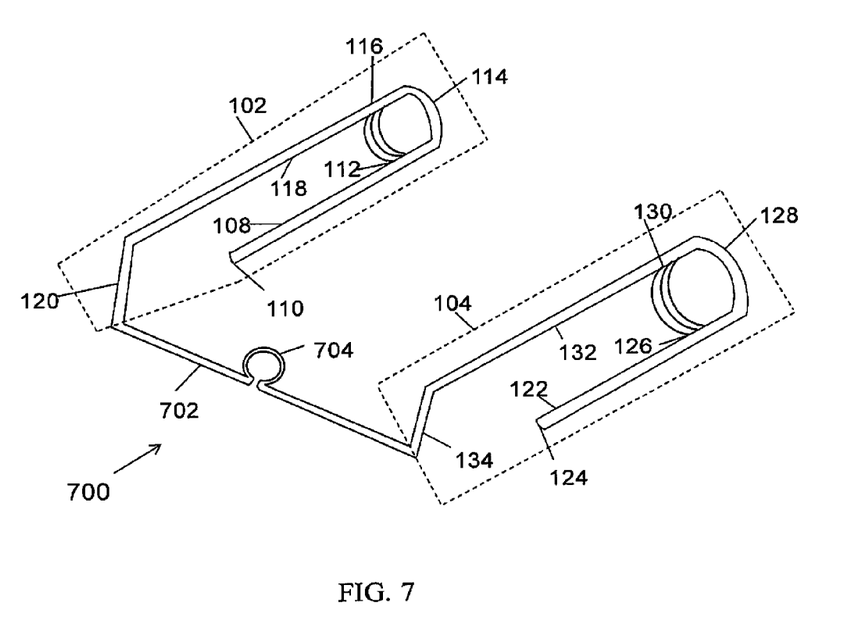
FIG. 7 illustrates another embodiment of the orthodontic separator shown on FIG. 1.

Referring to FIG. 7 an exemplary embodiment of the orthodontic separator 100 is shown, in which a connecting bar includes one or more loops. For example, a U-shaped loop 704 shown in the connecting bar 702 of the orthodontic separator 700. It will be readily apparent to those with ordinary skill in the art that the one or more loops can be of any other shape, for example, an omega loop, a circular loop and any other shaped loop usable to adjust the distance between two ends of the connecting bar 702, without deviating from the scope of the present invention. The connecting bar 702 with adjustable distance between the two ends ensures proper fitting of the orthodontic separator 700 to a tooth. It also helps in tight fit or increase in activation of the orthodontic separator 700 thereby preventing its dislodgement. The loop can also help in reducing the activation incase the orthodontic separator 700 is very tight.

Figure 8:
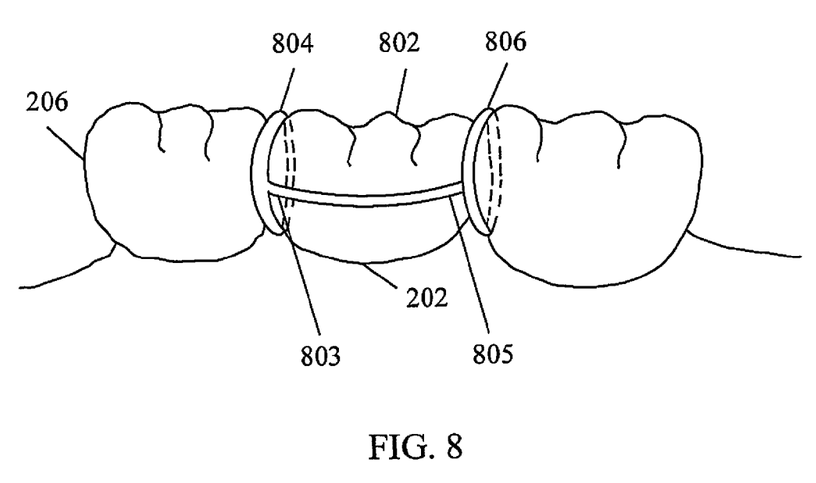
FIG. 8 illustrates another embodiment of individual orthodontic separators connected by a connecting bar.

Referring to FIG. 8 an exemplary embodiment of the present invention is shown, in which a connecting bar 802 is shown to connect individual orthodontic separators, i.e., a first individual orthodontic separator 804 and a second individual orthodontic separator 806 of elastomeric type. It will be readily apparent that the connecting bar 802 may be used to connect other types of individual orthodontic separators as well, for example, plastic separators, brass wire separators, metal spring devices and the like, thereby preventing the dislodgement of these individual orthodontic separators.

FIGS. 2 to 7 have illustrated those embodiments of the present invention in which the connecting bar is an integral part of the orthodontic separator. However, it will be readily apparent to those with an ordinary skill in the art that the present invention as defined by the claims also includes the embodiments in which the connecting bar can be used to connect any two individual orthodontic separators for example, plastic separators, brass wire separators, metal spring devices and the like, for example, FIG. 8 the connecting bar 802 connects two individual orthodontic separators 804 and 806 which is capable of separating both the mesial and distal aspects 600 and 601 of the tooth 202. Even in this embodiment the connecting bar 802 prevents dislodgement of the two individual orthodontic separators 804 and 806 of elastomeric type.

In an embodiment, a material of the connecting bar 802 can be the same as a material of the first individual orthodontic separator 804 and/or the second individual orthodontic separator 806. For example, the connecting bar 802 as well as the first individual orthodontic separator 804 and/or the second individual orthodontic separator 806 can be made of elastomeric materials. Examples of the material of the connecting bar 802, the first individual orthodontic separator 804 and/or the second individual orthodontic separator 806 can include, but are not limited to, a nickel titanium alloy, stainless steel, plastic, elastic, rubber, and a biocompatible dental material.

In another embodiment, the material of the connecting bar 802 can be different from the material of the first individual orthodontic separator 804 and/or the second individual orthodontic separator 806. For example, the connecting bar 802 may be made of a nickel titanium alloy while the first individual orthodontic separator 804 and/or the second individual orthodontic separator 806 may be made of an elastomeric material. Examples of the material of the connecting bar 802, the first individual orthodontic separator 804 and/or the second individual orthodontic separator 806 can include, but are not limited to, a nickel titanium alloy, stainless steel, plastic, elastic, rubber, and a biocompatible dental material.

Further, the connecting bar 802 may be connected to the first individual orthodontic separator 804 and/or the second individual orthodontic separator 806 through any means including, but not limited to, a hook, a clamp, a solder, casted and the like. In one embodiment, the connecting bar 802 may be connected to the first individual orthodontic separator 804 by simply fastening a first end 803 of the connecting bar 802 to the first individual orthodontic separator 804. Similarly, the connecting bar 802 may be connected to the second individual orthodontic separator 806 by simply fastening a second end 805 of the connecting bar 802 to the second individual orthodontic separator 806.

It will be apparent to those with ordinary skill in the art that various adjustments can be made in the orthodontic separator of various embodiments of the present invention after its construction/fabrication or in a preformed stage. The adjustments can be done according to the anatomy and morphology of the tooth. The adjustments can be incorporated in the preformed orthodontic separator or can be made during the insertion of orthodontic separator for proper fitting and for increasing or decreasing the activation of the orthodontic separator.

For example, the length of the free first arm end of the first separating unit and the free fourth arm end of the fourth arm of the second separating unit can be shortened by cutting the excess wire. Further the free first arm end and the free fourth arm end can be blunted or configured to form a compressed, flat and round edged loop hence preventing soft tissue trauma.

Further, the activation of the orthodontic separator can be increased by giving an upward bend towards occlusal direction in either or both of the first arm and the fourth arm. The activation of the orthodontic separator can be decreased by giving a downward bend towards gingival direction in either or both of the first arm and the fourth arm.

There can be one or more bends in either or both of the first arm and the fourth arm depending on required activation of the orthodontic separator and the anatomy of the tooth.

Bringing the first arm and the second arm of the first separating unit closer to each other can increase the activation of the first separating unit. Bringing the third arm and the fourth arm of the second separating unit closer to each other can increase the activation of the second separating unit. The activation can be decreased by taking the first arm and the second arm of the first separating unit away from each other. The activation can be decreased by taking the third arm and the fourth arm of the second separating unit away from each other.

If the junction of the second arm and the first vertical step of the first separating unit or the junction of the third arm and the second vertical step of the second separating unit is slightly occlusal, it can cause occlusal interference. Accordingly, a slight bend in the gingival direction can be given just behind the junction of the second arm and first vertical step and a similar slight bend can be given in the gingival direction just behind the junction of the third arm and the second vertical step to avoid the occlusal interference.

To increase the tight fit of either or both of the first separating unit and the second separating unit, a bend can be given in either or both of the first vertical step and second separating step to prevent the dislodgement of the orthodontic separator. Bend is given in opposite directions if the orthodontic separator is over tight.

To decrease the length of the connecting bar, its contour can be slightly increased and to increase the length of the connecting bar its contour can be slightly decreased. If the connecting bar has one or more loops, then these loops can be tightened or loosened to achieve the desired decrease or increase in the length of the connecting bar.

Various embodiments, as described above, provide an orthodontic separator, which has several advantages. One of the several advantages of some embodiments of this orthodontic separator is that it has self-secured connecting bar that connects the first separating unit and the second separating unit and prevents the movement and dislodgement of the orthodontic separator. The connecting bar prevents the movement and dislodgement of the orthodontic separator even after sufficient separation has been achieved thus avoiding the orthodontic separator to get embedded in the gingiva or being accidently swallowed by a patient.

While the invention has been disclosed in connection with the preferred embodiments shown and described in detail, various modifications and improvements thereon will become readily apparent to those skilled in the art. Accordingly, the spirit and scope of the present invention is not to be limited by the foregoing examples, but is to be understood in the broadest sense allowable by law.

What is claimed is:

1. An orthodontic separator to simultaneously separate mesial and distal aspect of a tooth, the orthodontic separator comprising:
    a first separating unit configured to be inserted between the mesial aspect of the tooth and a first adjacent tooth, the first separating unit comprising:

a first arm having a free end and a non-free end, the first arm being configured to be inserted between the tooth and the first adjacent tooth which is proximal to the mesial aspect;

a second arm extending in a direction substantially longitudinally parallel to the first arm, and on a first plane with the first arm;

a second separating unit configured to be inserted between the distal aspect of the tooth and a second adjacent tooth, the second separating unit comprising:

a third arm;

a fourth arm having a free end and a non-free end, the third arm extending from the non-free end of the fourth arm, and the fourth arm being configured to be inserted between the tooth and the second adjacent tooth which is proximal to the distal aspect; and the third arm extending in a direction substantially longitudinally parallel to the fourth arm on a second plane with the fourth arm;

a connecting bar attached between the first separating unit and the second separating unit, the connecting bar being configured to prevent dislodgement of the orthodontic separator from the tooth, and the insertion of the first separating unit and the second separating unit allowing the orthodontic separator to simultaneously separate the tooth and the adjacent tooth at each of the mesial and the distal aspects; and the first separating unit, the second separating unit, and the connecting bar are portions of a single monolithic piece.

2. The orthodontic separator according to claim 1, wherein the first separating unit further comprises a first spring coil initiating from the non-free end of the first arm; and a first vertical step initiating from a second arm end and ending at a first vertical step end; and the second arm initiates from the first spring coil end and ends at the second arm end.

3. The orthodontic separator according to claim 2, wherein the second separating unit further comprises a second vertical step initiating from a connecting bar end and ending at a second vertical step end, with the third arm initiating from the second vertical step end and ending at a third arm end; and a second spring coil initiating from the third arm end, with the fourth arm initiating from a second spring coil end.

4. The orthodontic separator according to claim 3, wherein the free fourth arm end is at least one of blunted and configured to form a compressed, flat and round edged loop, thereby preventing soft tissue trauma.

5. The orthodontic separator according to claim 2, wherein the first separating unit and the second separating unit being integrally connected with each other through the connecting bar which initiates from the first vertical step end and ends at a connecting bar end and wherein the first separating unit and the second separating unit are inter-changeable based on a location of the tooth in the oral cavity.

6. The orthodontic separator according to claim 5, wherein a distance between the first vertical step end and the connecting bar end of the connecting bar along a mesio-distal direction is substantially equal to a mesio-distal width of at least one of the lingual and the palatal aspect of the tooth.

7. The orthodontic separator according to claim 2, wherein the free first arm end is at least one of blunted and configured to form a compressed, flat and round edged loop, thereby preventing soft tissue trauma.

8. The orthodontic separator according to claim 1, wherein the connecting bar comprises one or more loops configured to be modulated to adjust a distance between the first separating unit and the second separating unit.

9. The orthodontic separator according to claim 1, wherein the connecting bar is at least one of pre-contoured and capable of being contoured to adapt to the tooth, thereby preventing the dislodgement of at least one of the first separating unit and second separating unit of the orthodontic separator.

10. The orthodontic separator according to claim 1, wherein material of the orthodontic separator is selected from the group comprising a nickel titanium alloy, stainless steel, plastic, elastic, rubber, and a biocompatible dental material.

11. The orthodontic separator according to claim 1, wherein material of the first separating unit, the second separating unit, and the connecting bar is selected from the group comprising of at least one of nickel titanium alloy, stainless steel, plastic, elastic, rubber, and a biocompatible dental material.

12. An orthodontic separator to simultaneously separate mesial and distal aspect of a tooth, the orthodontic separator comprising:

a first separating unit configured to be inserted between the mesial aspect of the tooth and a first adjacent tooth, the first separating unit comprising:

a first arm having a free end and a non-free end, the first arm being configured to be inserted between the tooth and the first adjacent tooth which is proximal to the mesial aspect;

a spring coil connected to the non-free end of the first arm; and a second arm extending from the spring coil in a direction substantially longitudinally parallel to the first arm and on a first plane with the first arm;

a second separating unit configured to be inserted between the distal aspect of the tooth and a second adjacent tooth, the second separating unit comprising:

a third arm;

a fourth arm having a free end and a non-free end, the third arm extending from the non-free end of the fourth arm, and the fourth arm being configured to be inserted between the tooth and the second adjacent tooth which is proximal to the distal aspect;

a spring coil connected to the non-free end of the fourth arm; and the third arm extending from the spring coil in a direction substantially longitudinally parallel to the fourth arm and on a second plane with the fourth arm; and a connecting bar attached between the first separating unit and the second separating unit, the connecting bar being configured to prevent dislodgement of the orthodontic separator from the tooth, and the insertion of the first separating unit and the second separating unit allowing the orthodontic separator to simultaneously separate the tooth and the adjacent tooth at each of the mesial and the distal aspects.

* * * * *